United States Patent [19]

Moore

[11] 4,058,896
[45] Nov. 22, 1977

[54] DENTAL ASPIRATOR TIP

[76] Inventor: Roland E. Moore, 2700 Tibbets No. 103, Bedford, Tex. 76021

[21] Appl. No.: 649,211

[22] Filed: Jan. 15, 1976

[51] Int. Cl.² .............................................. A61C 17/04
[52] U.S. Cl. ........................................................ 32/33
[58] Field of Search ........................................... 32/33

[56] References Cited

U.S. PATENT DOCUMENTS

| 2,130,406 | 9/1938 | Angell | 32/33 |
| 2,711,586 | 6/1955 | Groves | 32/33 |
| 3,768,477 | 10/1973 | Anders | 32/33 |

Primary Examiner—Robert Peshock
Attorney, Agent, or Firm—Charles W. McHugh

[57] ABSTRACT

An aspirator system for dentistry in which a hollow handle or holder has removable collector ends for insertion into a patient's mouth, which ends are sometimes called aspirator tips. In one embodiment of an aspirator tip, a relatively firm and bulbous end is provided adjacent the entrance to a bore in communication with a vacuum source; this tissue-contacting end has an open face and a generally hemispherical back. Within the open face lies a series of converging ridges, which are provided to trap solid particles having a size of about 2mm or greater. Since the ridges are completely exposed and there are no over-hanging ridges or the like, it is relatively easy to clean the face of the aspirator tip with a stiff brush or the like. The aspirator tip can be rotated at will with respect to the handle in order to achieve substantially any desired position within a patient's mouth. Also, aspirator tips of any of several designs may be interchangeably inserted into the handle. For convenience in manually adjusting the suction at the entrance of the bore, an aperture is provided on the handle at a location where it is easily covered by a person's finger.

13 Claims, 8 Drawing Figures

DENTAL ASPIRATOR TIP

This invention relates generally to an aspirating system for use in dentistry, and more particularly relates to aspirator tips for removing liquids from a patient's mouth.

In the field of dentistry, it is well known to employ a source of vacuum to create a low-pressure region in a patient's mouth for the purpose of removing liquids—including natural liquids (such as saliva) as well as liquids (such as water) supplied as coolants and lubricants for certain cutting tools. Also, there have been many proposals from time to time on an expeditious way to terminate the collector end of a vacuum line in a patient's mouth. Some have proposed that the collector head be relatively small, so that it does not interfere with the dentist's efforts to work in and around a tooth. Also, small collector heads are frequently more comfortable for a patient, since there is less bulk inserted into a patient's mouth. Too, relatively small collector heads can be particularly important when the patient is a child whose mouth is inherently small. On the other hand, a collector head which is too small may be uncomfortable to the patient, and it may damage tissue if the aspirator handle is inadvertently thrust too firmly against some tissue in the mouth. Also, making the collector head too small can concentrate the low-pressure region at the inlet end of the collector head in such a small area that tissue in the mouth is too readily pulled into the low-pressure opening; this frequently tends to stretch and/or pull tissue in an uncomfortable manner, and also tends to block the collector head so that it no longer serves its intended function in removing liquids. Thus, an aspirator tip which is too small can be uncomfortable to a patient, as well as being easily rendered inoperative; but an aspirator tip which is too large could perhaps be almost as bad. Example of prior art aspirator tips are found in U.S. Pat. Nos. 3,768,477 to Anders et al, 3,864,831 to Drake, and 3,890,712 to Lopez.

In addition to the beneficial removal of liquids from a patient's mouth, an aspirator tip sometimes removes solids from the mouth, too. Such solids include tooth fragments, amalgum particles, or other solid objects that may be in a patient's mouth. In order to preclude damage to the vacuum pump that is providing suction for the aspirator tip, there will typically be a filter and/or screen located between the tip and the vacuum pump, usually immediately ahead of the vacuum pump. Hence, if a solid particle having a substantial size is sucked through the aspirator tip, someone must usually disassemble at least a portion of the aspirator equipment to gain access to the filter and/or screen that hopefully has trapped the solid particle. If a nurse or dental technician is mechanically inclined, perhaps she could stop her work and clean the filter. Otherwise, the dentist—who should be doing more productive things—may be diverted from his skilled work to partially disassemble a machine so as to clean a filter and recover the solid particles. While it would be desirable to capture as many of these solid particles as possible at the collector end of the aspirator system, it is also true that attention must be given to sanitation of any instrument which is inserted into a patient's mouth. Hence, any collector head which is to be used in dentistry should have a configuration that fosters frequent and effective cleaning. Too, there should be no apertures or hidden crevices or grooves which are incapable of being physically cleaned with a brush or probe or the like. Accordingly, it is an object of this invention to provide a collector end for an aspirator system which overcomes the deficiencies of known prior systems.

It is a further object to provide an aspirator system which can be used with two or more different types and/or shapes of collector heads, e.g., a head for routine dental procedures and also a different head for surgical operations.

Still another object is to provide an aspirator tip wherein the user (typically a dental assistant) can manually control the amount of suction at the entrance of a suction tube by alternately opening and closing a prepared orifice on the side of the aspirator tip. These and other objects, as well as the distinct advantages of this invention, will be apparent from a reading of the specification with reference to the attached drawings, in which.

Figure 1:
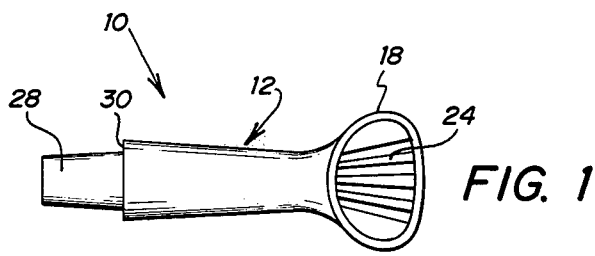
FIG. 1 is a top view taken perpendicular to the longitudinal axis of an aspirator tip of the invention.
Figure 2:
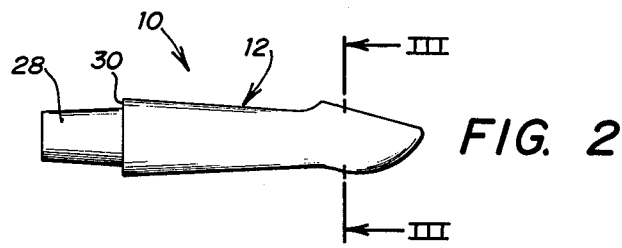
FIG. 2 is a side view of the aspirator tip shown in FIG. 1.
Figure 3:
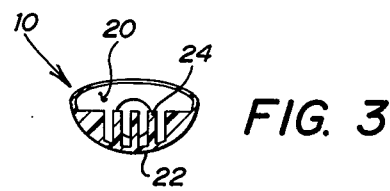
FIG. 3 is a cross-sectional view of the collector end of the tip of FIG. 1, taken in the plane defined by numerals III—III of FIG. 2.

With initial reference to FIG. 1, a dental aspirator tip 10 is shown with a rigid shank 12 having a longitudinal bore 14 which is adapted to be connected to a source of vacuum 16. At the forward end of the shank 12 is a so-called collector head, i.e., a head through which material enters the system in response to vacuum created by source 16. The collector head of this invention comprises a firm and relatively large tissue-contacting member 18 having a width which is appreciably larger than the diameter of the shank 12. This tissue-contacting member 18 may be integrally formed with the shank 12, or it may be affixed thereto in any suitable manner so as to be held rigidly at the forward end of the shank. If the member 18 is not integrally formed with the shank 12, the two elements must be attached in such a way as to permit the passage of liquids into the bore entrance.

The tissue-contacting member 18 has an open face 20 and a closed back 22; the closed back preferably has a generally hemispherical configuration, such that the member 18 has a somewhat bulbous appearance when viewed from the rear. One reason for having an open face 20 (for receiving liquids) opposite a hemispherical back 22 is to insure that tissue in the mouth will be pushed out of the way as the aspirator tip is pressed far enough against the tissue so that liquids are drawn into the bore 14. That is, to the extent that the closed back 22 pushes tissue out of the way, it takes up the slack or "stretches" the tissue and more nearly insures that the tissue lying immediately adjacent the edge of the open face 20 will not have enough resiliency to be pulled into the open face when a vacuum is established in longitudinal bore 14.

Within the tissue-contacting member 18 and ahead of the entrance to the bore 14 is provided a rigid blocking means, which is preferably one or more rigid bars 24 that extend in the same general direction as the longitudinal bore; at least one of the bars extends far enough toward the entrance of said bore as to partially block the same. The object, of course, is to permit the passage of all liquids into the entrance to said bore, but to block the passage of certain solids. The blocking means is ideally intended to trap any solid particle having a diameter of about 2 millimeters. Of course, for the blocking means 24 to have any efficacy, it must be relatively rigid, or at least firm enough to remain in a fixed position in spite of a pressure differential established by a vacuum pump, etc. An example of a permissible material for aspirator tip 10 would be hard rubber, but a preferred material is a rigid plastic such as an acetal copolymer sold by Celanese Plastics Co. under the trademark Celcon.

With regard to dimensions of a preferred embodiment of the aspirator tip 10, the longitudinal bore 14 will have a diameter of about 7mm. The width of the tissue-contacting member 18 will be about 25mm; thus, the width of member 18 is about three times the diameter of the bore 14. The open face 20 will have a length (measured in the same direction as the longitudinal axis of the bore 14) of about 15mm. The distance between respective ridges 24 will be about 1mm, and the width of each of the ridges will be about 1.5mm. A total length for this particular aspirator tip 10 is about 65mm—which is relatively short, but which is serviceable in view of a holder or handle 26 which is adapted to be connected with the tip 10. Of course, these dimensions are intended to describe only the preferred embodiment, and some deviation from these dimensions could be made without adversely affecting certain facets of the invention.

In order to affect connection with the holder 26, the shank 12 has a relieved portion 28 having a length of about 14mm and a taper of about 3°. The tapered portion 28, of course, is adapted to mate with a counterbored end portion 32 on holder 26; and holder 26 also has a longitudinal bore which is in communication with bore 14 when the elements 10, 26 are joined together. A vertical shoulder 30 is provided on the shank 12 to preclude a person from twisting the elements 10, 26 together so tightly that there arises the risk of fracturing one or both of the elements—or connecting them together so tightly that tools might be required to separate them. The counterbored end 32 of holder or handle 26 is capable of accepting any aspirator tip which has a suitable tapered portion. Hence, a nurse or dental technician can readily switch from one aspirator tip to another, merely by imparting a slight twist to the assembled pieces.

Figure 4:
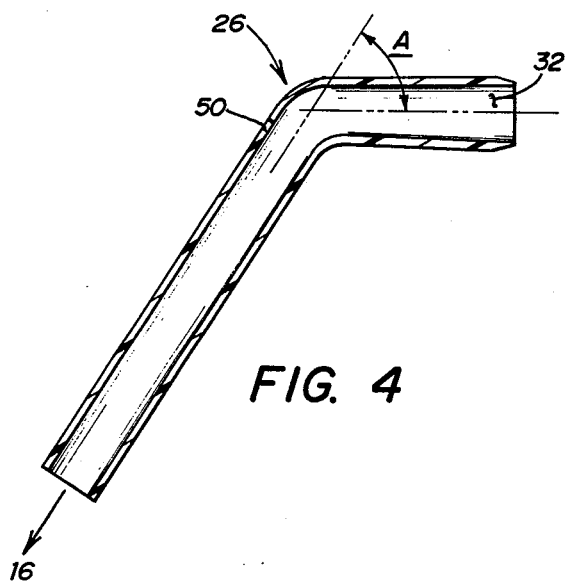
FIG. 4 is a longitudinal, sectional view of a holder or handle for holding an aspirator tip such as the one shown in FIG. 1.
Figure 5:
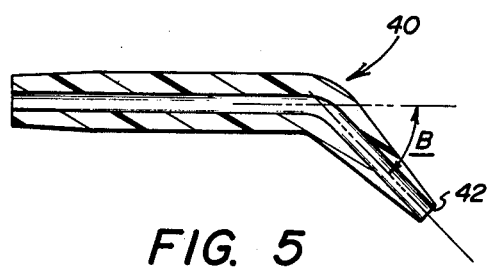
FIG. 5 is a cross-sectional view of another aspirator tip.
Figure 6:
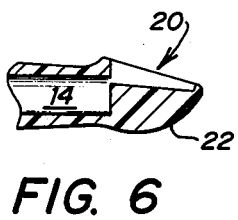
FIG. 6 is a fragmentary cross-sectional view of the collector end of an aspirator tip, taken in a direction perpendicular to FIG. 3.

Another aspirator tip is shown in FIG. 5, and this tip 40 is commonly referred to as a "surgical" aspirator tip, because—for one reason—it has a much smaller head and it therefore can be more readily placed immediately adjacent a portion of the patient's mouth where the removal of liquids is critical. Also, it has a smaller opening at the entrance of the bore, so a more substantial low pressure region is established without any change in the pump's operation. The forward end of the surgical tip 40 is preferably bent downward with respect to the longitudinal axis of the bore, so as to form an angle B of about 45°. Referring again to FIG. 4, the forward end of handle 26 is also preferably bent with respect to the main portion of the handle; this inclination is represented in FIG. 4 by the angle A. The angle A is preferably about 60°, because it has been found that such an angle fosters the efficient use of an aspirator tip by the dentist (or his assistant) while also minimizing any discomfort to the patient. The use of a bent handle also contributes to maximizing the space available to the dentist immediately in front of the patient's mouth, so that the dentist can more readily position his hands for working without interfering with the hands of an assistant who is holding the aspirator handle 26.

As with the aspirator tip 10, the rearward end of the tip 40 has a taper to foster ready connection with the counterbored end of handle 26. That taper is preferably about 3° to 5°, such that the angle C in FIG. 5 would be about 6° to 10°. The length of the "drooped" or forward end of the tip 40 is preferably about 1 inch, and the length of the longer portion (including the tapered region that mates with the holder 26) is preferably about 2 inches. The forward end of the tip 40 has a relatively small diameter, e.g., 4mm, while the inner diameter of the bore is approximately 3mm; hence, the surgical tip 40 has a relatively thin wall at its forward end.

Figure 7:
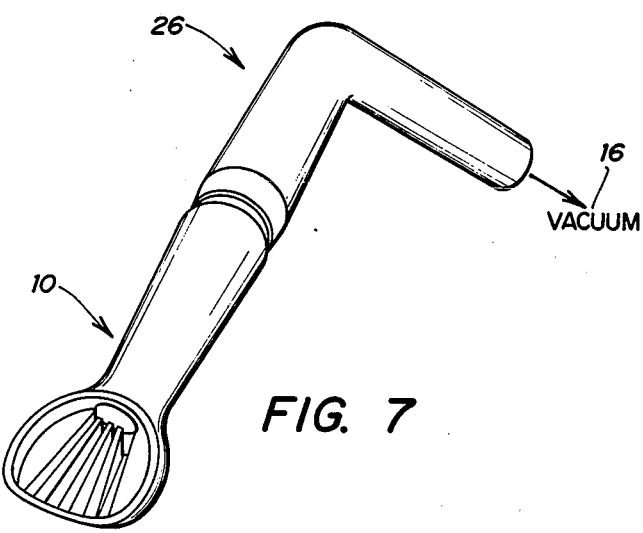
FIG. 7 is a perspective view of an aspirator tip as shown in FIG. 1 when combined with a handle as shown in FIG. 4.
Figure 8:
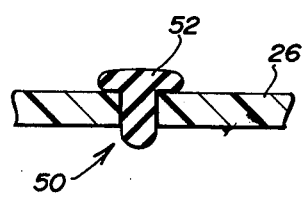
FIG. 8 is a fragmentary sectional view of the air-bleeding aperture of a holder (shown with a rubber plug therein).

In operation of the aspirator system disclosed herein, the dentist's assistant would typically connect the handle 26 with a flexible tube leading to a vacuum pump of any conventional design. Next, a given aspirator tip would be selected to comport with the job at hand. For routine work such as preparing a tooth for a filling, etc., an aspirator tip such as tip 10 would likely be selected. The tip 10 would normally be connected with the handle 26 with an orientation such as shown in FIG. 7, wherein the open face of the bulbous end would be pointed upward (or away) from the tissue which is to be contacted. As the dental assistant gently presses the bulbous end against the tissue in the mouth, the tissue which is contacted will yield in response to such pressure. The word "stretch" could perhaps be fairly employed in describing this movement of tissue; but "stretch" to some people might indicate that there is substantial tension in the contacted tissue, and this might not always be true. Whether the bulbous end 18 actually imparts tension in the tissue, or merely takes up slack, is not really the critical matter. What is critical (as far as constituting a design criterion), and what is provided by the tissue contacting member 18, is that liquids may be drawn into the bore 14 without simultaneously pulling loose tissue toward the entrance of said bore. If any solid particles within the mouth should also be drawn by the suction pump into the open face of the collector head 18, such solid particles may be caught within the space between two adjacent converging ridges 24. If the particles are too large to become wedged between two adjacent ridges, they will usually come to rest on top of a couple of the ridges adjacent the entrance to the bore 14. As long as the vacuum pump is in operation, such relatively large particles may be held there by a pressure differential; removing the aspirator tip 10 from the patient's mouth and subsequently disconnecting the tip 10 from the handle 26 would then permit such particles to immediately fall away from the position in which they were held by the vacuum.

Any solid particles that became wedged or trapped between two adjacent ridges can be readily disengaged through use of a simple pick which is a customary part of every dentist's equipment. Whenever time is available to an assistant, the interior portion of the bulbous end 18 can also be readily cleaned with a tool such as a toothbrush having relatively stiff bristles. With relatively little work, then, the aspirator tip 10 can be quickly and reliably cleaned of any foreign matter. No sophisticated cleaning implement is required; nor is it likely that one or more apertures might be accidentally overlooked during a cleaning step—as might be the case with some prior-art aspirator tips. Too, the cleaning strokes of a brush, etc., can be relatively straight strokes, and essentially all of the portions to be scrubbed or brushed can be contacted during the course of a single brushing stroke. After the surface portions of the member 18 have been vigorously brushed, the tip 10 can then be immersed in an antiseptic solution, agitated, and quickly returned to service. Since there are no tissue-contacting apertures and the like, there should be no risk or accidentally transferring any germs from one persons's mouth to another's mough—if the few easy cleaning steps described herein are followed.

If it is desired to employ a different aspirator tip, a simple "twist and pull" action will separate the tip 10 from the holder 26, whereupon a different aspirator tip, such as tip 40, may be inserted into the counterbore 32. Assuming that the surgical tip 40 has been connected with the holder 26, if there is too much vacuum at the forward end 42, the technician who is gripping the holder 26 can simply remove a finger which has been covering hold 50. This will automatically increase the area through which air is being supplied to the vacuum pump, and it will therefore reduce the suction at the forward end 42. Manually covering the hole 50 again will automatically increase the vacuum at the forward end of any aspirator tip—without requiring any adjustment of the vacuum pump. If the opportunity to manually affect the obtainable vacuum at the collecting end of an aspirator tip is not desired, it would be possible—of course—to temporarily (or permanently) insert a small rubber plug 52 or the like into the aperture 50. The relatively large head of such a plug 52 would prevent it from being drawn into the vacuum pump, but it could still be readily removed at will, so as to restore the opportunity for manual vacuum control. It would be expected that an aperture 50 having a diameter of about one-eight inch would be able to provide an appropriate variation in the normal vacuum established by the pump controls (e.g., about 15 inches of mercury) by virtue of being alernately opened and closed.

While only the preferred embodiments of the invention have been disclosed in great detail herein, it will be apparent to those skilled in the art that modifications thereof can be made without departing from the spirit of the invention. For example, the aspirator tips 10, 40 have been described as preferably made of Celcon; but probably most any rigid thermoplastic or thermosetting resin that is safe for insertion into a person's mouth could be similiarly employed. And, the resin from which a tip 10, 40 is made need not even be permanently stable at sterilizing temperatures or in the presence of certain antiseptic cleaning agents—because it would be possible to treat the tips as disposable after use on a single patient. Also, the angles formed by the forward or "drooped" ends of the surgical tips might be varied somewhat from the specific angles described hereinabove—although the preferred angles shown in the drawing and described herein have been found to provide more efficiency as well as comfort for the dentist, his assistant and the patient.

What is claimed is:

1. An oral aspirator tip, comprising:
   a. a rigid shank having a longitudinal bore adapted to be connected to a source of vacuum;
   b. a firm and relatively large tissue-contacting member being generally spoon-shaped and having an open face and a closed back, and having a width appreciably larger than the diameter of the shank, with the tissue-contacting member being affixed to the forward end of the shank in such a way as to permit the passage of liquids through the open face and into the bore entrance; and
   c. rigid blocking means lying internally of the spoon-shaped member and ahead of the entrance to said bore, for permitting the passage of all liquids but blocking the passage of certain solids into said bore, and the blocking means including at least two elevated ridges integrally formed with and extending forwardly from the enclosed back of the spoon-shaped member, with said ridges being oriented in the same general direction as the longitudinal bore, and the ends of the ridges which are near the bore entrance being closer together than their remote ends, such that solid particles passing internally of the spoon-shaped member may become wedged between the converging walls of the ridges, and the near end of at least one of the ridges partially blocking the entrance to said bore in such a way as to provide at least two flowpaths for liquids passing into said bore, whereby the collection of any one solid particle between the ridges will not block the entrance to the longitudinal bore.

2. The aspirator tip as claimed in claim 1 wherein the closed back of the tissue-contacting member has a generally hemispherical configuration, and the open face of the tissue-contacting member is generally planar.

3. The aspirator tip as claimed in claim 1 wherein said blocking means constitutes a set of linear converging ridges which extend from the remote end of the tissue-contacting member to near the entrance of the bore, and which at least partially obstruct the entrance to said bore, and all interior surfaces of said member being accessible through the open face of the tissue-contacting member in order to permit all of said surfaces to be scrubbed with a cleaning brush, whereby there are no hidden crevices or apertures which are not cleanable and which might accumulate waste so as to introduce the risk of transferring germs from one patient to another.

4. An oral aspirator tip, comprising:
   a. a rigid shank having a longitudinal bore adapted to be connected to a source of vacuum;
   b. a firm and relatively large tissue-contacting member having an open face and a closed back, and having a width appreciably larger than the diameter of the shank, with the tissue-contacting member being affixed to the forward end of the shank in such a way as to permit the passage of liquids through the open face and into the bore entrance; and
   c. rigid blocking means lying within the tissue-contacting member and ahead of the entrance to said bore, for permitting the passage of all liquids but blocking the passage of certain solids, and the blocking means being sized so as to catch solid particles having a dimension larger than two millimeters, and wherein said blocking means comprises at least three converging ridges which extend from the remote end of the tissue-contacting member to near the entrance of the bore, with the included angle between adjacent ridges being about 5°.

5. The oral aspirator tip as claimed in claim 1 wherein the tissue-contacting member is a bulbous member of generally hemispherical shape, and the width of said member is about three times the diameter of said bore, and the height of said member is only about twice the diameter of said bore.

6. A dental aspirator tip, comprising:
 a. a relatively short and rigid shank having a longitudinal bore, with said shank having a first, open end and a second end which is tapered to foster selective connection with a handle which is in communication with a source of vacuum;
 b. a rigid and relatively bulbous tissue-contacting member rigidly fixed to the first end of said shank, with said member having an open and substantially flat face, and having a substantially hemispherical and closed back, and the width of said tissue-contacting member being appreciably larger than the diameter of said shank; and
 c. a plurality of firm ridges bounded by the tissue-contacting member, with said ridges each having a length and a width, with the length of the ridges being measured in the same general direction as the longitudinal axis of the shank, and the width of said ridges being about 1.5mm.

7. The dental aspirator tip as claimed in claim 6 wherein the plurality of ridges converge toward the first end of the shank.

8. The dental aspirator tip as claimed in claim 7 wherein the angle between any two adjacent ridges is on the order of 5°.

9. The dental aspirator tip as claimed in claim 6 wherein the planes defined by respective ones of the ridges are each perpendicular to the plane of the face, whereby brushing strokes applied parallel to the face can clean between respective ridges.

10. The dental aspirator tip as claimed in claim 6 wherein the depth of the ridges exceeds the width thereof.

11. The dental aspirator tip as claimed in claim 6 wherein the gap between adjacent ridges is about 1 millimeter at the first end of the shank.

12. The dental aspirator tip as claimed in claim 6 wherein the ridges are permanently secured to the tissue-contacting member.

13. A dental aspirator device, comprising:
 a. a relatively short and rigid tubular shank having first and second ends and a longitudinal bore therebetween, with the second end having an external taper of about 6° for a length in excess of 10 millimeters, with said tapered end being adapted to mate with a tubular handle which is in communication with a source of vacuum, and the length of said shank being about 5 centimeters, and the material from which the shank is made having the general physical characteristics of a rigid thermoplastic or thermosetting resin;
 b. a rigid and relatively bulbous tissue-contacting member rigidly connected to the first end of said shank, and said member having an open face which defines a plane that makes an angle of about 15° with respect to the longitudinal axis of the shank, and the back of said tissue-contacting member being closed such that fluids which are to be drawn into the bore of said shank will pass through the open face, and the back being convex such that gently pressing the member against tissue in the mouth will tend to eliminate any slack in said tissue, and the size of said face being appreciably larger than the diameter of said bore; and
 c. at least two ridges permanently secured within the tissue-contacting member and ahead of the entrance to said bore, with said ridges being inclined with respect to each other so as to converge toward the entrance end of said bore, and the included angle between adjacent ridges being about 5°, and at least one of said ridges extending close enough to said bore entrance as to partially block the same, whereby certain solid particles which may be drawn through the face of the tissue-contacting member by virtue of a pressure differential can be trapped by the blocking ridges and thereby be prevented from entering the bore, with the size of said certain trapped particles being on the order of 2 millimeters.

* * * * *